(12) United States Patent
Weber

(10) Patent No.: US 9,622,898 B1
(45) Date of Patent: Apr. 18, 2017

(54) ANKLE BRACE

(71) Applicant: Charles W. Weber, Las Vegas, NV (US)

(72) Inventor: Charles W. Weber, Las Vegas, NV (US)

( * ) Notice: Subject to any disclaimer, the term of this patent is extended or adjusted under 35 U.S.C. 154(b) by 0 days.

(21) Appl. No.: 14/073,710

(22) Filed: Nov. 6, 2013

Related U.S. Application Data

(60) Provisional application No. 61/722,905, filed on Nov. 6, 2012.

(51) Int. Cl.
*A61F 5/01* (2006.01)
*A43B 7/20* (2006.01)
*A61F 5/058* (2006.01)

(52) U.S. Cl.
CPC .............. *A61F 5/0111* (2013.01); *A43B 7/20* (2013.01); *A61F 5/0104* (2013.01); *A61F 5/0585* (2013.01)

(58) Field of Classification Search
CPC ........ A61F 5/0111; A61F 5/0113; A43B 3/16; A43B 3/163; A43B 3/18; A43B 7/14; A43B 7/18; A43B 7/20
USPC .......... 602/27–29, 65; 128/882; 36/2 R, 140, 36/144
See application file for complete search history.

(56) References Cited

U.S. PATENT DOCUMENTS

| 4,719,926 | A | | 1/1988 | Nelson |
| 4,841,957 | A | | 6/1989 | Wooten et al. |
| 4,977,891 | A | | 12/1990 | Grim |
| 5,031,607 | A | | 7/1991 | Peters |
| 5,250,021 | A | | 10/1993 | Chang |
| 5,368,551 | A | | 11/1994 | Zuckerman |
| 5,501,659 | A | | 3/1996 | Morris et al. |
| 5,584,799 | A | * | 12/1996 | Gray ................................ 602/5 |
| 5,776,090 | A | * | 7/1998 | Bergmann et al. ............. 602/28 |
| 7,727,174 | B2 | * | 6/2010 | Chang et al. .................... 602/28 |
| 2004/0030275 | A1 | * | 2/2004 | Morinaka ............. A61F 5/0125 602/27 |
| 2006/0217649 | A1 | * | 9/2006 | Rabe .................... A61F 5/0111 602/27 |

* cited by examiner

*Primary Examiner* — Keri J Nelson
(74) *Attorney, Agent, or Firm* — Kenehan & Lambertsen, Ltd; John C Lambertsen

(57) ABSTRACT

An ankle brace received by a footwear boot prevents extension or flexion of the foot while walking. The ankle brace includes a pair of side trusses joined at the top by a shin band and at the bottom by a metatarsal band. When placed on the boot the shin band extends over and across a lower front portion of the shin bone, the metatarsal band extends over the toes and lower foot, and the pair of trusses extend along the inside and outside in a parallel manner from the front of the foot to the ankle and up to the lower shin. A heel strap and heel cup attached to the pair of trusses extends around and receives the back of the boot, retaining the brace in place against the boot.

14 Claims, 2 Drawing Sheets

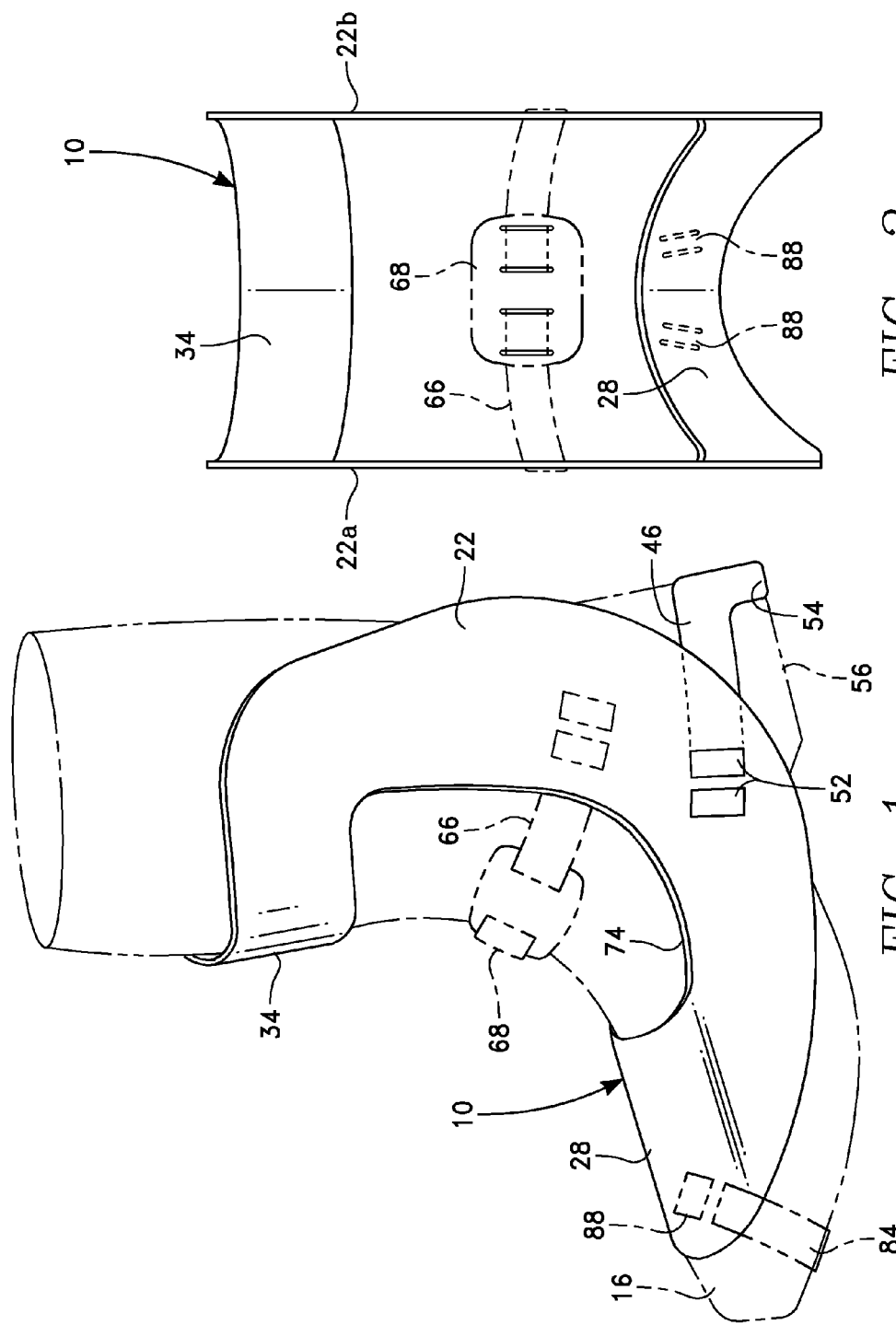

ANKLE BRACE

RELATED APPLICATIONS

The present application claims the benefit of priority under 35 USC §119(e) to U.S. Provisional Application No. 61/722,905, filed on Nov. 6, 2012, which is incorporated by reference herein for all that it contains.

BACKGROUND OF THE INVENTION

Field of the Invention

The present invention relates to orthotic device, and more specifically to a brace used to immobilize a joint. More specifically, the present invention relates to a foot brace that is placed over a conventional footwear boot to prevent extension or flexion of the foot, enabling use of the boot while protecting the Achilles tendon or ankle during healing.

Description of the Related Art

Traditionally, severe heel and ankle injuries were first treated by encasement in a heavy plaster cast until healing was complete. Subsequent medical studies suggested the desirability of having the patient begin walking at an early stage of rehabilitation. The heavy plaster casts were modified by adding load bearing inserts to enable ambulatory patient movement. Although encouraged by their doctor and therapist to begin walking, these heavy plaster casts were not pleasant for the patient—in addition to the various discomforts of rigid casts, the weight of the cast when walking tended to cause fatigue and place strains on the affected leg muscles.

The development of plastics offered brace shops the ability to provide strong, rugged braces that were easily molded. Continued innovation in such braces resulted in the creation of various types of "walkers." Depending upon their design and foot/leg retention mechanisms, the majority of walkers were successful in substituting for the initially-used rigid casts during rehabilitation. These plastic walkers were much lighter than the rigid plaster casts, offering considerable improvement in patient mobility and agility. Additionally, the walker could be removed at bedtime and during inactive periods, allowing the patient to bring some level of normalcy during this recovery period.

The majority of such walkers provide a "foot bed" to support the foot and a pair of struts extending upwardly from the base to provide support to the ankle and lower leg. Straps extending from the base secure the foot and various straps wrapping around the braces and lower leg maintain the lower leg in position between the struts. Some walkers provide for a removable foot and ankle encasing boot providing the foot some protection during use of the walker.

Ankle and heel injuries can require months of healing time before recovery is complete. The placement of some level of weight-bearing load on the injured joint assists in the healing process for the bones, ligaments, and tendons. Of course, the application of too much weight or an appropriate weight but too quickly or in the wrong direction can reinjure the joint, extending the rehabilitation process. The "walker" braces enable mobility; however, they do not provide much in the way of an enclosure for protecting the foot. A need exists to permit patients to progress towards more conventional footwear while maintaining protection over the healing joint and related tissue.

SUMMARY OF THE INVENTION

A foot brace in accordance with aspects of embodiments of the present invention is able to fit around all types of boots and shoes. When used with high-top boots the brace is placed over and secured to the front of the shin and on the top of the foot, with a strap placed around the heel securing the brace to the foot.

The present invention can also be used with other types of footwear. For example, when used on a lower-top shoe the upper curved band is enlarged (made wider) and is provided padding—both of which are designed to protect the shin, and a strap around the back of the leg is also preferably provided. By such design changes a user is permitted to wear such type of foot protection as is required for the user's employment, hobby or sport of choice.

In a further aspect of the present invention the foot brace can incorporate a suspension/dampened hinge that permits infinitely varying degrees of articulation/weight to bear on the ankle joint and Achilles tendon as the injury heals.

An aspect of embodiments in accordance with the present invention is an ankle brace comprising: a pair of trusses for extending along both the inside and outside in a parallel manner from the front of the foot to the ankle and up to the lower shin; a metatarsal band attached to both of said pair of trusses for extending over the toes and lower foot; a shin band attached to both of said pair of trusses for extending over and across a lower, front portion of the shinbone; and a heel strap attached to said pair of trusses for extending around and receiving the back of a boot heel, whereby placement of the ankle brace over the front of a footwear boot and attachment of the heel strap to the back of the boot heel prevents extension or flexion of the foot.

Another aspect of embodiments in accordance with the present invention is an ankle brace adapted to be received by a footwear boot for inhibiting extension and flexion of a foot comprising: a unitary member made of a substantially rigid material including a pair of trusses laterally extending along both the inside and outside in a parallel manner from the front of the foot to the ankle and up to the lower shin and including at its upper end a shin band adapted to extend over and across a lower, front portion of the shin bone and including at its lower end a metatarsal band adapted to extend over the toes and lower foot; and a heel strap attached to said unitary member and adapted to extend around and receive the back of a boot heel.

These and other objects, aspects, and features of the present invention will be better understood from the following description of embodiments when read in conjunction with the appended drawing figures.

It is to be understood that the invention is not limited in its application to the details of construction and the arrangement of components described hereinafter and illustrated in the drawing figures. Those skilled in the art will recognize that various modifications can be made without departing from the scope of the invention.

BRIEF DESCRIPTION OF THE DRAWINGS

Embodiments in accordance with the present invention are described below in connection with the accompanying drawing sheets.

FIG. 1 is a side perspective view, with portions shown in phantom, of an ankle brace in accordance with the present invention.

FIG. 2 is a rear elevation view, with portions shown in phantom, of the ankle brace of FIG. 1 in accordance with the present invention.

DESCRIPTION OF THE PRESENTLY PREFERRED EMBODIMENTS

Figure 4:
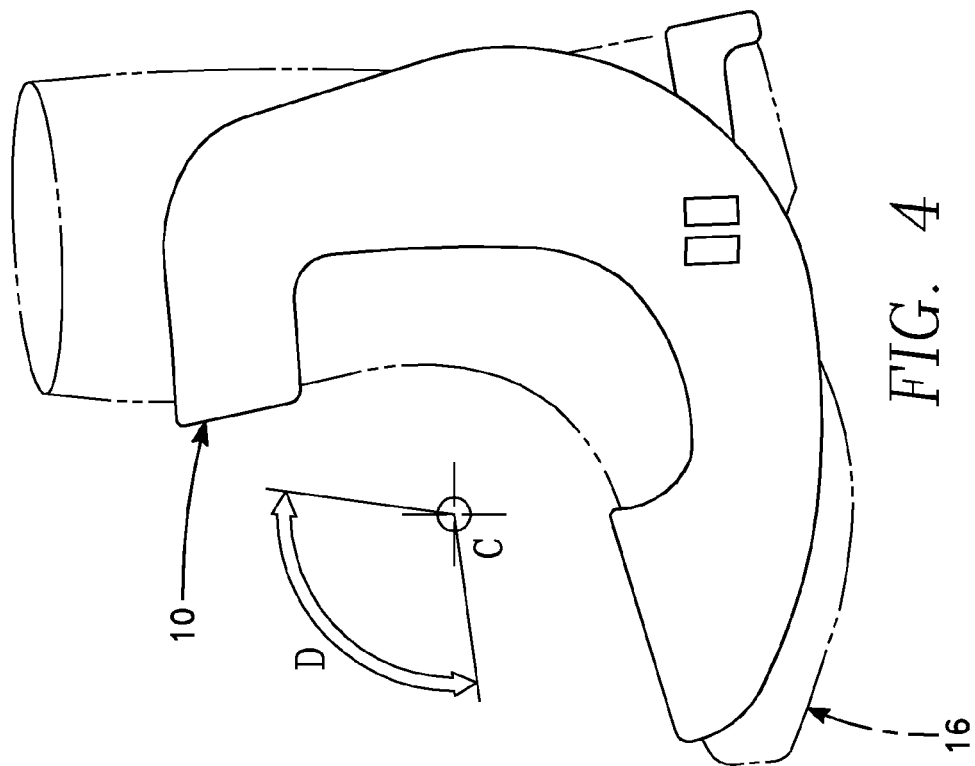
FIG. 4 is a schematic view, similar to FIG. 3, of a lower leg and attached foot where attachment of the ankle brace of FIG. 1 results in the translational movement of the location of flexion away from the ankle.

The ankle brace is disclosed herein with respect to exemplary embodiments. The embodiments are disclosed for illustration of the ankle brace and a manner of operation, and are not limiting except as defined in the appended claims.

Reference is now made to the drawings wherein like structures refer to like parts throughout. In FIG. 1 an ankle brace 10 is placed over and secured to a boot 16 placed on the foot of a patient (not shown in the Figures), providing support for many of the ankle weight-bearing bones, ligaments, and tendons. The ankle brace 10 includes a pair of lateral trusses 22 (the ankle brace 10 is substantially symmetric and only one of the pair of trusses is shown in FIG. 1—while the pair of trusses 22a, 22b are shown in FIG. 2). Each of the trusses 22a, 22b extend on a separate side of the foot and leg, along both the medial border and the lateral border (see FIG. 2), from a location adjacent the toes, curving upwardly to a location on the lower leg that is several inches above the ankle.

The pair of trusses 22 connect to one-another at each end using a pair of curved metal bands, a first, metatarsal band 28 is located over the toes and lower foot, and a second, shin band 34 extends over and across a lower, front portion of the tibia or shinbone. The pair of bands 28, 34 are preferably of a unitary construction, fabricated out of a number of possible materials, including stainless steel, molded steel, aluminum, and carbon fiber/fiberglass.

As is shown in FIGS. 1 and 2 the pair of trusses 22 are L- or crescent-shaped and extend along both the inside (medial border) and outside (lateral border) in a parallel manner, from the front of the foot, to the ankle malleolus, and then up to the lower shin. This pair of trusses 22 in a sense forms a bridge extending from the mid/lower shin to the upper foot, from mid-arch to the tip of the toes. This pair of trusses 22 connect across the top, in front of the shin, using a curved metal band that conforms to the shape of the shin over which it extends. At the bottom, the pair of trusses 22 connect using a curved metal band that extends over the top of the foot, above the toes, toe joints, and the adjacent, forward portion of the metatarsals.

A heel strap 46, fabricated out of strong material, such as KEVLAR® brand para-aramid synthetic fiber, is also provided, and extends through a pair of heel strap slots 52 formed in each of the pair of trusses 22 in a mid-truss location. A heel cup 54 is attached to the heal strap 46 and is positioned on the strap to extend around and receive the back (and an adjacent portion of the bottom) of the boot heel 56 when in use. The heel strap 46 and heel cup 54 maintain the ankle and foot in position against both of the pair of side trusses 22 to prevent unwanted foot/ankle movement when weight is placed upon the ball of the foot.

Additional security and placement of the foot within the ankle brace 10 may optionally be obtained by use of a front strap 66 and buckle 68. The front strap extends across a front opening 74 overlying the top of the patient's foot and formed between the pair of trusses 22 and the lower metatarsal band 28 and the upper shin band 34. A pair of front strap slots 78 receive the front strap 66 on each of the pair of trusses 22. Also optional is a toe strap 84 that is received by toe strap slots 88 formed in the front of the metatarsal band 28. When used the toe strap 84 further secures the ankle brace 10 to the boot 16.

In FIG. 1 the heel strap 46 is shown extending from mid-brace (connecting the "corners" of the two L-shaped trusses 22) and, with the heel cup 54, attaches the ankle brace 10 to the foot. The resulting bridge structure of the ankle brace 10 acts to transfer body weight from the ball of the foot to the lower shin. In this manner no extension or flexion of the foot (also termed plantar flexion and dorsiflexion) is required while walking (or otherwise) and thus no stretching forces are applied to the Achilles tendon or ankle joint or ligaments.

Figure 3:
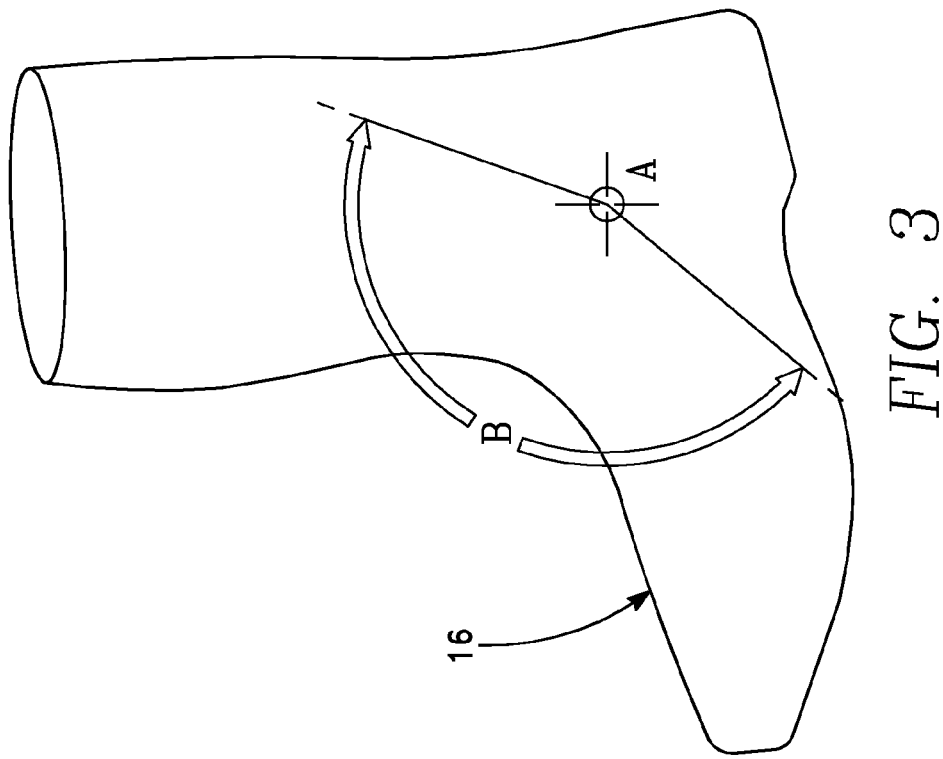
FIG. 3 is a schematic view of a lower leg and attached foot illustrating the location of flexion to be at or closely adjacent to the ankle when walking.

The benefits provided by the present invention are schematically illustrated in FIGS. 3 and 4. In FIG. 3 an unbraced foot is shown pivoting about the ankle (Pivot A) as the ball of the foot pushes off against the ground, causing the foot to bend at the ankle and propel the leg and body forward, while the other foot lands on the heel, the ankle bending as the ball of the other foot makes contact with the ground before it, too, pushes off against the ground as the person continues to walk forward. This heel-ball-heel extension/flexion movement (Arrow B) of the foot all pivots about the ankle.

In FIG. 4 the installed ankle brace results in the pivot point being moved forward from the ankle (Pivot C), with the extension and flexion forces transferred from the ball of the foot directly to the shin (Arrow D), keeping the ankle immobile—with no bending force placed on the ankle. The foot and lower shin remain in this fixed-angle relation defined by the pair of trusses, which are in turn secured to the boot by the heel strap and front strap.

In this regard it is noted that the heel of the foot is required to bare (vertical) weight; however, no side-to-side or front-to-back strains are placed upon the ankle joint or ligaments. The tibia and fibula rest directly on the heel bone with only cartilage between them. If the injury is to one of those, obviously another type of brace is required. However, where injury is to the ankle or one (or more) of the associated tendons or ligaments, the present brace provides a "bridge" transferring weight around the injured ankle, providing mobility using a normal, unaltered boot.

My invention has been disclosed in terms of a preferred embodiment thereof, which provides an ankle brace that is of great novelty and utility. Various changes, modifications, and alterations in the teachings of the present invention may be contemplated by those skilled in the art without departing from the intended spirit and scope thereof. It is intended that the present invention encompass such changes and modifications.

What is claimed is:

1. An ankle brace comprising:
   a pair of trusses for extending along both a medial border and lateral border in a parallel manner from the front of the foot to the ankle malleolus and up to the lower shin, wherein each of said pair of trusses is configured to overlie the protruding portion of the ankle malleolus and extends posteriorly thereof;
   a metatarsal band attached to both of said pair of trusses for extending over the toes and lower foot;
   a shin band attached to both of said pair of trusses for extending over and across a lower, front portion of the shinbone, wherein said pair of trusses, said metatarsal band, and said shin band are fabricated out of a substantially rigid material and wherein a front opening is formed between each of the pair of trusses and between the metatarsal band and the shin band, the front opening for overlying the dorsal surface of the ankle and for extending from the lower foot to the lower front position of the shinbone; and a heel strap attached to said pair of trusses for extending around and receiving the back of a boot heel, whereby placement of the ankle brace over the front of a footwear boot and attachment of the heel strap to the back of the boot heel prevents extension or flexion of the foot.

2. The ankle brace of claim 1, and further comprising a heel cup attached to said heel strap and configured to extend around and receive the back and adjacent portion of the bottom of a boot heel.

3. The ankle brace of claim 2, wherein said pair of trusses, said metatarsal band, and said shin band form a continuous outer surface.

4. The ankle brace of claim 3, wherein said pair of trusses, said metatarsal band, and said shin band are of a unitary construction.

5. The ankle brace of claim 4, and further comprising a front strap attached to each of said pair of trusses and extending across said front opening.

6. The ankle brace of claim 4, and further comprising a toe strap attached to said metatarsal band for extending around and receiving the toe of a boot.

7. An ankle brace adapted to be received by a footwear boot for inhibiting extension and flexion of a foot comprising:

a unitary member made of a substantially rigid material including a pair of trusses configured to laterally extend along both a medial border and lateral border in a parallel manner from the front of the foot to the ankle malleolus and up to the lower shin and including at its upper end a shin band adapted to extend over and across a lower, front portion of the shin bone and including at its lower end a metatarsal band adapted to extend over the toes and lower foot, wherein a front opening is formed in said unitary member between each of the pair of trusses and between the metatarsal band and the shin band, the front opening adapted to overlie the dorsal surface of the ankle and adapted to extend from the lower foot to the lower front portion of the shin bone, and wherein each of said pair of trusses is configured to overlie the protruding portion of the ankle malleolus and extends posteriorly thereof; and a heel strap attached to said unitary member and adapted to extend around and receive the back of a boot heel.

8. The ankle brace of claim 7, and further comprising a heel cup attached to said heel strap and configured to extend around and receive the back and adjacent portion of the bottom of a boot heel.

9. The ankle brace of claim 8, and further comprising a front strap attached to said unitary member and extending across said front opening.

10. The ankle brace of claim 8, and further comprising a toe strap attached to said metatarsal band for extending around and receiving the toe of a boot.

11. An ankle brace comprising:

a pair of trusses for extending along both a medial border and lateral border in a parallel manner from the front of the foot to the ankle malleolus and up to the lower shin wherein the ankle malleolus defines a pivot location relative to a heel-ball-heel extension/flexion movement of an unbraced foot, and wherein each of said pair of trusses is configured to overlie said pivot location and extends posteriorly thereof;

a metatarsal band attached to both of said pair of trusses for extending over the toes and lower foot;

a shin band attached to both of said pair of trusses for extending over and across a lower, front portion of the shinbone, wherein said pair of trusses, said metatarsal band, and said shin band are fabricated out of a substantially rigid material and wherein a front opening is formed between each of the pair of trusses and between the metatarsal band and the shin band, the front opening for overlying the dorsal surface of the ankle and for extending from the lower foot to the lower front position of the shinbone; and a heel strap attached to said pair of trusses for extending around and receiving the back of a boot heel, whereby placement of the ankle brace over the front of a footwear boot and attachment of the heel strap to the back of the boot heel prevents extension or flexion of the foot.

12. The ankle brace of claim 11, and further comprising a heel cup attached to said heel strap and configured to extend around and receive the back and adjacent portion of the bottom of a boot heel.

13. The ankle brace of claim 12, wherein said pair of trusses, said metatarsal band, and said shin band form a continuous outer surface.

14. The ankle brace of claim 13, wherein said pair of trusses, said metatarsal band, and said shin band are of a unitary construction.

* * * * *